United States Patent
Knaack et al.

(10) Patent No.: US 10,322,209 B2
(45) Date of Patent: *Jun. 18, 2019

(54) POLYURETHANES FOR OSTEOIMPLANTS

(71) Applicant: Warsaw Orthopedic, Inc., Warsaw, IN (US)

(72) Inventors: David Knaack, Summit, NJ (US); John Winterbottom, Dundee, MI (US); David R. Kaes, Toms River, NJ (US); Todd Boyce, Collierville, TN (US); Lawrence A. Shimp, Burlington, WI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/974,146

(22) Filed: May 8, 2018

(65) Prior Publication Data

US 2018/0250442 A1    Sep. 6, 2018

Related U.S. Application Data

(63) Continuation of application No. 15/643,137, filed on Jul. 6, 2017, now Pat. No. 9,993,579, which is a continuation of application No. 15/144,139, filed on May 2, 2016, now Pat. No. 9,789,223, which is a continuation of application No. 13/867,689, filed on Apr. 22, 2013, now Pat. No. 9,327,052, which is a continuation of application No. 13/181,715, filed on Jul. 13, 2011, now Pat. No. 8,425,893, which is a continuation of application No. 10/771,736, filed on Feb. 4, 2004, now Pat. No. 8,002,843.

(60) Provisional application No. 60/444,759, filed on Feb. 4, 2003.

(51) Int. Cl.
| | | |
|---|---|---|
| A61L 27/18 | (2006.01) |
| A61L 27/36 | (2006.01) |
| A61L 27/46 | (2006.01) |
| C08G 18/10 | (2006.01) |
| C08G 18/36 | (2006.01) |
| C08G 18/38 | (2006.01) |
| C08G 18/64 | (2006.01) |
| C08G 18/73 | (2006.01) |
| C08G 18/77 | (2006.01) |
| C08G 18/79 | (2006.01) |
| A61L 27/54 | (2006.01) |
| A61L 27/58 | (2006.01) |
| C08L 75/04 | (2006.01) |

(52) U.S. Cl.
CPC .......... *A61L 27/3608* (2013.01); *A61L 27/18* (2013.01); *A61L 27/46* (2013.01); *A61L 27/54* (2013.01); *A61L 27/58* (2013.01); *C08G 18/10* (2013.01); *C08G 18/36* (2013.01); *C08G 18/3878* (2013.01); *C08G 18/3882* (2013.01); *C08G 18/6484* (2013.01); *C08G 18/73* (2013.01); *C08G 18/771* (2013.01); *C08G 18/798* (2013.01); *C08L 75/04* (2013.01); *A61L 2300/414* (2013.01); *A61L 2300/426* (2013.01); *A61L 2430/02* (2013.01); *C08G 2230/00* (2013.01)

(58) Field of Classification Search
CPC ............ A61K 47/48215; A61K 9/0024; A61L 27/3608; A61L 27/18
USPC .............................................. 424/78.27, 422
See application file for complete search history.

(56) References Cited

U.S. PATENT DOCUMENTS

| | | | |
|---|---|---|---|
| 2,882,249 A | 4/1959 | Posnansky | ................... 525/111 |
| 4,477,604 A | 10/1984 | Oechsle, III | |
| 4,570,270 A | 2/1986 | Oechsle, III | |
| 4,698,318 A | 10/1987 | Vogel et al. | |
| 4,829,099 A | 5/1989 | Fuller et al. | |
| 4,880,610 A | 11/1989 | Constantz | |
| RE33,161 E | 2/1990 | Brown et al. | |
| 4,902,508 A | 2/1990 | Badylak et al. | |
| RE33,221 E | 5/1990 | Brown et al. | |
| 5,034,059 A | 7/1991 | Constantz | |
| 5,047,031 A | 9/1991 | Constantz | |
| 5,053,212 A | 10/1991 | Constantz | |
| 5,116,550 A | 5/1992 | Perkins | |
| 5,129,905 A | 7/1992 | Constantz | |
| 5,149,368 A | 9/1992 | Liu et al. | |
| 5,243,038 A | 9/1993 | Ferrari et al. | |
| 5,262,166 A | 11/1993 | Liu et al. | |
| 5,263,984 A | 11/1993 | Li et al. | |
| 5,266,608 A | 11/1993 | Katz et al. | |
| 5,336,264 A | 8/1994 | Constantz et al. | |

(Continued)

FOREIGN PATENT DOCUMENTS

| | | |
|---|---|---|
| DE | 19546367 A1 | 6/1997 |
| DE | 19546371 A1 | 6/1997 |

(Continued)

OTHER PUBLICATIONS

Reexamination of Knaack et al., U.S. Pat. No. 7,985,414 (Apr. 12, 2012) Application/Control No. 90/012,932.
Determination of Ex-parte Reexam (Aug. 30, 2013) Application/Control No. 90/012,932.
Agarwal et al., "Biodegradable Urethanes for Biomedical Applications", Ch. 7 of Tissue Engineering and Biodegradable Equivalents, Lewandrowski et al., ed., 2002 Marcel Dekker, Inc. New York.
Bruin et al., Design and synthesis of biodegradable poly(esterurethane) elastomer networks composed of non-toxic building blocks, Makromol. Chern., Rapid Commun. vol. 9 Issue 8, 1988, pp. 589-594.

(Continued)

*Primary Examiner* — Raymond J Henley, III

(57) ABSTRACT

Biological-based polyurethanes and methods of making the same. The polyurethanes are formed by reacting a biodegradable polyisocyanate (such as lysine diisocyanate) with an optionally hydroxylated biomolecule to form polyurethane. The polymers formed may be combined with ceramic and/or bone particles to form a composite, which may be used as an osteoimplant.

20 Claims, No Drawings

(56) References Cited

U.S. PATENT DOCUMENTS

| | | | |
|---|---|---|---|
| 5,462,722 A | 10/1995 | Liu et al. | |
| 5,507,810 A | 4/1996 | Prewett et al. | |
| 5,525,148 A | 6/1996 | Chow et al. | |
| 5,542,973 A | 8/1996 | Chow et al. | |
| 5,578,086 A | 11/1996 | Prescott | |
| 5,605,713 A | 2/1997 | Boltong et al. | |
| 5,607,269 A | 3/1997 | Dowd et al. | |
| 5,650,176 A | 7/1997 | Lee et al. | |
| 5,717,006 A | 2/1998 | Daculsi et al. | |
| 5,800,899 A | 9/1998 | Sandvig | |
| 6,001,394 A | 12/1999 | Daculsi et al. | |
| 6,002,065 A | 12/1999 | Constantz et al. | |
| 6,123,731 A | 9/2000 | Boyce et al. | 623/23.63 |
| 6,127,442 A | 10/2000 | Sulzbach et al. | |
| 6,206,957 B1 | 3/2001 | Driessens et al. | |
| 6,294,187 B1 | 9/2001 | Boyce et al. | |
| 6,306,177 B1 | 10/2001 | Felt et al. | |
| 6,696,073 B2 | 2/2004 | Boyce et al. | 424/422 |
| 8,002,843 B2 | 8/2011 | Knaack et al. | |
| 8,425,893 B2 * | 4/2013 | Knaack | A61L 27/18 424/422 |
| 9,327,052 B2 * | 5/2016 | Knaack | A61L 27/18 |
| 9,789,223 B2 * | 10/2017 | Knaack | A61L 27/18 |
| 2003/0039676 A1 | 2/2003 | Boyce et al. | |
| 2003/0138473 A1 | 7/2003 | Koblish et al. | |
| 2003/0144743 A1 | 7/2003 | Edwards et al. | |
| 2004/0024457 A1 | 2/2004 | Boyce et al. | |
| 2004/0146543 A1 | 7/2004 | Shimp et al. | |
| 2005/0008620 A1 | 1/2005 | Shimp et al. | |
| 2005/0008672 A1 | 1/2005 | Winterbottom et al. | |
| 2005/0013793 A1 | 1/2005 | Beckman et al. | |
| 2005/0027033 A1 | 2/2005 | Knaack et al. | |
| 2005/0031578 A1 | 2/2005 | Deslauriers et al. | |
| 2005/0070913 A1 | 3/2005 | Milbocker et al. | |
| 2005/0238683 A1 | 10/2005 | Adhikari et al. | |
| 2006/0216323 A1 | 9/2006 | Knaack et al. | |

FOREIGN PATENT DOCUMENTS

| | | |
|---|---|---|
| EP | 1162222 A2 | 12/2001 |
| JP | 04-129695 | 9/1993 |
| JP | 04129695 | 9/1993 |
| JP | 2002088247 A | 3/2002 |
| WO | 1994009048 A1 | 4/1994 |
| WO | 199515776 A1 | 6/1995 |
| WO | WO 1995/15776 | 6/1995 |
| WO | 199911296 A2 | 3/1999 |
| WO | WO 1999/11296 | 3/1999 |
| WO | 200050102 A1 | 8/2000 |
| WO | WO 2000/50102 | 8/2000 |
| WO | 200202156 A2 | 1/2002 |
| WO | WO 2002/02156 A2 | 1/2002 |
| WO | 2004009227 A2 | 1/2004 |
| WO | 2004065450 A2 | 8/2004 |
| WO | 2004065450 A3 | 8/2004 |
| WO | WO 2004/065450 | 8/2004 |

OTHER PUBLICATIONS

Gorna et al., Preparation, degradation, and calcification of biodegradable polyurethane foams for bone graft sustitutes, Journal of Biomedical Materials Research Part A vol. 67A Issue 3, pp. 817-827 first published online Oct. 17, 2003.
International Search Report PCT/2004/001200 dated Sep. 30, 2004.
Supplementary European Search Report Application No. EP 07 71 8273.
Tissue Engineering and Biodegradable Equivalents Scientific and Clinical Applications, Lewandrowski et al., Copyright 2002, Marcel Dekker, Inc., see chapter 7.
Reexamination of Knaack et al., U.S. Pat. No. 7,985,414 (Apr. 12, 2012) Application/Control No. 90/012,251.
Determination of Ex-parte Reexam (May 16, 2012) Application/Control No. 90/012,251.
Agrawal (eds.), et al., "Synthetic Bioabsorbable Polymers for Implants", Gorna and Gogolewski on Novel Polyurethanes, p. 39-57, Jul. 2000.
Gunatillake, et al., "Biodegradable Synthetic Polymers for Tissue Engineering", European Cells and Materials, 5: 1-16,2003.
Lewandrowski, et al., "Kinetics of cortical bone demineralization: Controlled demineralization—a new method for modifying cortical bone allografts", J. Biomed. Materials Res., 31: 365-72, 1996.
Morlock, et al., "Duration and frequency of every day activities in total hip patients", J. Biomech., 34: 873-81,2001.
Reddi, et al., "Biochemical sequences in the transformation of normal fibroblasts in adolescent rats", Proc. Nat. Acad. Sci. USA, 69:1601-5, 1972.
Urist, "A morphogenetic matrix for differentiation of bone tissue", Calcif. Tissue Res., Suppl: 98-101, 1970.
Urist, "Bone: formation by autoinduction", Science, 150(698); 893-9,1965.
Weiner, "Biologically-derived or biomimetic materials such as those identified in Lowenstam HA", On Biomineralization, Oxford University Press, 234,1989.
Zhang, et al., "A new peptide-based urethane polymer: synthesis, biodegradation, and potential to support cell growth in vitro", Biomaterials, 21:1247-58, 2000.
Zhang, et al., "Synthesis, Biodegradability, and Biocompatibility of Lysine Diisocyanate-Glucose Polymers", Tis. Eng., 8(5): 771-85, 2002.
Zhang, et al., "Three-dimensional biocompatible ascorbic acid-containing scaffold for bone tissue engineering," Tissue Engineering, 9(6): 1143-57, 2003.
International Application No. PCT/US04/03233 International Search Report.
International Application No. PCT/US04/03233 Written Opinion.
Rich, et al., Lactic Acid Based PEU/HA and PEU/BCP Composites: Dynamic Mechanical Characterization of Hydrolysis, Department of Chemical Technology, Polymer Technology; Helsinki University of Technology.
Rich, Jaana, In Vitro Characterization of Bioresorbable polymers and composites for drug delivery and bone replacement, Acta Polytechnica Scandinavica, Chemical Technology Series No. 289, Espoo 2002, 47 pp. Published by the Finnish Academies of Technology, ISBN 951-666-609-9, ISSN 1239-0518.
Gogolewski, S. Nonmetallic Materials for Bone Substitutes, European Cells and Materials vol. 1 suppl 2 2001 pp. 54-55.
Bruin et al., Design and synthesis of biodegradable poly(ester-urethane) elastomer networks composed of non-toxic building blocks, Makromol. Chem., Rapid Commun. vol. 9 Issue 8, 1988, pp. 589-594.
Gorna et al., Preparation, degradation, and calcification of biodegradable polyurethane foams for bone graft sustitutes, Journal of Biomedical Materials Research Part A vol. 67A Issue 3, pp. 817-827 first published online Oct. 17, 2003.
Zhang, et al., Synthesis, Biodegradability, and Biocompatibility of Lysine Diisocyanate-Glucose Polymers, Tissue Engineering, vol. 8, No. 5, 2002, pp. 771-785.
ReExamination of David Knack, U.S. Pat. No. 7,985,414 issued Jul. 26, 2011 from U.S. Appl. No. 11/336,127, filed Jan. 19, 2006.
ReExamination U.S. Appl. No. 90/012,932, filed Jul. 26, 2013.
Decision on Ex Parte ReExamination of David Knack, U.S. Pat. No. 7,985,414 issued Jul. 26, 2011. ReExamination Certificate No. 7,985,414 C2 issued May 9, 2014.
Gorna et al., Preparation, degradation, and calcification of biodegradable polyurethane foams for bone graft substitutes, Journal of Biomedical Materials Research Part A, vol. 67A Issue 3, pp. 817-827 first published online Oct. 17, 2003.

* cited by examiner ated immune responses from the recipient. There is
also a need to provide composite grafts of suitable shape and
size that maximize the utility of the graft tissue.

POLYURETHANES FOR OSTEOIMPLANTS

This application is a continuation of and claims priority to U.S. application Ser. No. 15/643,137, filed on Jul. 6, 2017, now U.S. Pat. No. 9,993,579, which is a continuation of U.S. application Ser. No. 15/144,139, filed on May 2, 2016, now U.S. Pat. No. 9,789,223, which is a continuation of U.S. application Ser. No. 13/867,689, filed on Apr. 22, 2013, now U.S. Pat. No. 9,327,052, which is a continuation of U.S. application Ser. No. 13/181,715, filed on Jul. 13, 2011, now U.S. Pat. No. 8,425,893, which is a continuation of U.S. application Ser. No. 10/771,736, filed on Feb. 4, 2004, now U.S. Pat. No. 8,002,843, which claims priority to U.S. Provisional Application No. 60/444,759, filed on Feb. 4, 2003, the contents of which are incorporated herein by reference in their entirety.

BACKGROUND OF THE INVENTION

Vertebrate bone is a composite material composed of hydroxyapatite, collagen, and a variety of noncollagenous proteins, as well as embedded and adherent cells. Vertebrate bone can be processed into an implantable biomaterial, such as an allograft, for example, by removing the cells, leaving behind the mineral and extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone or may alternatively be processed into soft, moldable or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implant site due to stress shielding. Furthermore, metal implants are permanent and unable to participate in physiological remodeling.

Following implantation, the host's own bone remodeling capabilities permit some bone grafts and certain bone substitute materials to remodel into endogenous bone that in most cases is indistinguishable from the host's own bone. In general, however, it is a limitation of allograft bone that larger allografts do not completely remodel, and residual allograft bone may persist at the graft site for many years or indefinitely, potentially acting as a stress riser and a possible fracture site. The use of bone grafts is further limited by the availability of tissue with the appropriate shape and size, as well as the desired mechanical strength and degradation rate.

U.S. Pat. No. 6,294,187, the contents of which are incorporated herein by reference, describes methods for preparing composites including allogenic bone for use in load bearing orthopedic applications. It is desirable to increase the strength of bone-reinforced composites by increasing the strength of the matrix material while retaining the resorbable properties of the matrix. Furthermore, there is a need for a novel resorbable polymer capable of synergistically interacting with bone to make a true composite having mechanical characteristics of both bone and polymer. There is also a need to develop resorbable polymers for the production of bone/polymer composites where the polymer itself has osteopromotive or osteopermissive properties and contributes to osteointegration and remodeling of the composite. It is also desirable to develop implants that do not elicit undesirable immune responses from the recipient. There is also a need to provide composite grafts of suitable shape and size that maximize the utility of the graft tissue.

SUMMARY OF THE INVENTION

In one aspect, the invention is a biodegradable polyurethane composite. The composite comprises a polyurethane matrix and a reinforcement embedded in the matrix. The polyurethane matrix is formed by reaction of a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with an optionally hydroxylated biomolecule (e.g., a phospholipids, fatty acid, cholesterol, polysaccharide, starch, or a combination or modified form of any of the above) to form a biodegradable polymer, while the reinforcement comprises bone or a bone substitute (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these). The polyurethane may be cross-linked. The polyisocyanate may be a diisocyanate. The biomolecule may be lecithin. The composite may comprise other materials, such as polycaprolactone, or a biomolecule, bioactive agent, or small molecule (e.g., lectins, growth factors, immunosuppresives, or chemoattractants). The reinforcement may be present in amounts of at least 10, 30, 50, or 70 weight percent. The composite may have a wet compressive strength in excess of that of the polyurethane alone, or may have a wet compressive strength of at least 3 MPa, 10 MPa, 50 MPa, 75 MPa, or 100 MPa. The composite may be able to survive at least $10^5$ fatigue cycles at 3 MPa when wet, or $10^6$ fatigue cycles at 25 MPa when wet. The creep rate may be less than 15% in 24 hours at 3 MPa when wet, or less than 10% in 24 hours at 25 MPa when wet. The polyurethane may degrade at a rate sufficient to permit generation of new tissue at an in vivo implantation site. The degradation rate may be about 5%, 10%, or 25% of the original composite weight per month in vivo. The maximum resolved strength in shear, compression, or tension may be at least 3 MPa.

In another aspect, the invention is a biodegradable polyurethane. The polyurethane is formed by the reaction of a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with a mixture of optionally hydroxylated biomolecules. The mixture of optionally hydroxylated biomolecules includes polysaccharides and lipids or phospholipids, and may include lecithin. The polyurethane may be cross-linked. The polyisocyanate may be a diisocyanate. The polyurethane may comprise other materials, such as polycaprolactone, or a biomolecule, bioactive agent, or small molecule (e.g., lectins, growth factors, immunosuppresives, or chemoattractants). The polyurethane may also comprise a reinforcement (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these), which may be at least 10, 30, 50, or 70 weight percent of the composite so formed. The composite may have a wet compressive strength in excess of that of the polyurethane alone. The polyurethane may have a wet compressive strength of at least 3 MPa, 10 MPa, 50 MPa, 75 MPa, or 100 MPa. The polyurethane may be able to survive at least $10^5$ fatigue cycles at 3 MPa when wet, or $10^6$ fatigue cycles at 25 MPa when wet. The creep rate may be less than 15% in 24 hours at 3 MPa when wet, or less than 10% in 24 hours at 25 MPa when wet. The polyurethane may degrade at a rate sufficient to permit generation of new tissue at an in vivo implantation site. The degradation rate may be about 5%, 10%, or 25% of the original polyurethane weight per month in vivo. The maximum resolved strength in shear, compression, or tension may be at least 3 MPa.

In still another aspect, the invention is a nonresorbable, biocompatible polyurethane. The polyurethane is formed by reaction of a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates), with a polysaccharide biomolecule, and optionally also with a lipid or phospholipid. The polyurethane may be cross-linked. The polyisocyanate may be a diisocyanate, and bay react with a hydroxyl group on the biomolecule. The polyurethane may comprise other materials, such as polycaprolactone, or a biomolecule, bioactive agent, or small molecule (e.g., lectins, growth factors, immunosuppresives, or chemoattractants). The polyurethane may also comprise a reinforcement (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these), which may be at least 10, 30, 50, or 70 weight percent of the composite so formed. The composite may have a wet compressive strength in excess of that of the polyurethane alone. The polyurethane may have a wet compressive strength of at least 3 MPa, 10 MPa, 50 MPa, 75 MPa, or 100 MPa. The polyurethane may be able to survive at least $10^5$ fatigue cycles at 3 MPa when wet, or $10^6$ fatigue cycles at 25 MPa when wet. The creep rate may be less than 15% in 24 hours at 3 MPa when wet, or less than 10% in 24 hours at 25 MPa when wet. The polyurethane may degrade at a rate sufficient to permit generation of new tissue at an in vivo implantation site. The degradation rate may be about 5%, 10%, or 25% of the original polyurethane weight per month in vivo. The maximum resolved strength in shear, compression, or tension may be at least 3 MPa.

In yet another aspect, the invention is a method of making a polyurethane composite. The method comprises reacting a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with an optionally hydroxylated biomolecule (e.g., a phospholipids, fatty acid, cholesterol, polysaccharide, starch, or a combination or modified form of any of the above) and a reinforcement comprising bone or a bone substitute (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these), to form a biodegradable polymer matrix having particles of reinforcement embedded therein. Additional substances such as bioactive agents, biomolecules, or small molecules (e.g., lectins, growth factors, immunosuppresives, or chemoattractants) may also be added to the composite. Reacting may include adding a chain extender or exposing the reactants to a catalyst (e.g., mild bases, strong bases, sodium hydroxide, sodium acetate, tin-containing compounds, or triethylenediamine 1,4-diaza (2,2,2) bicyclooctane), and may be carried out for a time period in the range from about one minute to about four hours. It may also include reacting the polyisocyanate and the biomolecule to form a prepolymer, mixing the prepolymer with the reinforcement to form a precomposite, and reacting the precomposite to form a polyurethane composite (e.g., by cross-linking).

In a further aspect, the invention is a method of making a biodegradable polyurethane, by reacting a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with a mixture of optionally hydroxylated biomolecules, comprising polysaccharides and lipids or phospholipids. The method may further comprise adding a reinforcement (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these) to the polyurethane to form a composite material, for example by reacting the polyisocyanate and the biomolecule to form a prepolymer, mixing the prepolymer with the reinforcement to form a precomposite, and reacting the precomposite (e.g., by cross-linking). Other substances, such as a bioactive agent, biomolecule, or small molecule (e.g., lectins, growth factors, immunosuppresives, or chemoattractants) may also be added to the polymer. Reacting may include adding a chain extender or exposing the reactants to a catalyst (e.g., mild bases, strong bases, sodium hydroxide, sodium acetate, tin-containing compounds, or triethylenediamine 1,4-diaza(2,2,2) bicyclooctane), and may be carried out for a time period in the range from about one minute to about four hours.

In yet a further aspect, the invention is a method of making a nonresorbable, biocompatible polyurethane polymer, by reacting a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with a biomolecule comprising a polysaccharide. The method may further comprise adding a reinforcement (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these) to the polyurethane to form a composite material, for example by reacting the polyisocyanate and the biomolecule to form a prepolymer, mixing the prepolymer with the reinforcement to form a precomposite, and reacting the precomposite (e.g., by cross-linking). Other substances, such as a bioactive agent, biomolecule, or small molecule (e.g., lectins, growth factors, immunosuppresives, or chemoattractants) may also be added to the polymer. Reacting may include adding a chain extender or exposing the reactants to a catalyst (e.g., mild bases, strong bases, sodium hydroxide, sodium acetate, tin-containing compounds, or triethylenediamine 1,4-diaza(2,2,2) bicyclooctane), and may be carried out for a time period in the range from about one minute to about four hours.

Definitions

The term "biomolecules," as used herein, refers to classes of molecules (e.g., proteins, amino acids, peptides, polynucleotides, nucleotides, carbohydrates, sugars, lipids, nucleoproteins, glycoproteins, lipoproteins, steroids, etc.) that are commonly found in cells and tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The term "biocompatible," as used herein, is intended to describe materials that, upon administration in vivo, do not induce undesirable long term effects.

As used herein, "biodegradable," "bioerodable," or "resorbable" materials are materials that degrade under physiological conditions to form a product that can be metabolized or excreted without damage to organs. Biodegradable materials are not necessarily hydrolytically degradable and may require enzymatic action to fully degrade. Biodegradable materials also include materials that are broken down within cells.

"Polynucleotide," "nucleic acid," or "oligonucleotide": The terms "polynucleotide," "nucleic acid," or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide," "peptide," or "protein" comprises a string of at least two amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide," "carbohydrate," "oligosaccharide," or "starch" refer to a polymer of sugars. The terms "polysaccharide" and "carbohydrate" may be used interchangeably to mean a sugar polymer of any length. "Oligosaccharide" generally refers to a relatively low molecular weight polymer, while "starch" typically refers to a higher molecular weight polymer. The polymer may include natural sugars (e.g., glucose, fructose, galactose, mannose, arabinose, ribose, and xylose) and/or modified sugars (e.g., 2"-fluororibose, 2'-deoxyribose, and hexose). Polysaccharides may or may not be crosslinked.

"Small molecule": As used herein, the term "small molecule" is used to refer to molecules, whether naturally-occurring or artificially created (e.g., via chemical synthesis), that have a relatively low molecular weight. Typically, small molecules have a molecular weight of less than about 5000 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present invention.

As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants (e.g., cyclosporine), anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, antihypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, antidepressants, anti-psychotic substances, anti-emetics, imaging agents, specific targeting agents, neurotransmitters, proteins, cell response modifiers, and vaccines. In a certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe," edited by Von Keemann et al., Stuttgart/New York, 1987, all of which are incorporated herein by reference.

As used herein, "anti-AIDS substances" are substances used to treat or prevent Autoimmune Deficiency Syndrome (AIDS). Examples of such substances include CD4,3'-azido-3'-deoxythymidine (AZT), 9-(2-hydroxyethoxymethyl)-guanine acyclovir, phosphonoformic acid, 1-adamantanamine, peptide T, and 2',3' dideoxycytidine.

As used herein, "anti-cancer substances" are substances used to treat or prevent cancer. Examples of such substances include methotrexate, cisplatin, prednisone, hydroxyprogesterone, medroxyprogesterone acetate, megestrol acetate, diethylstilbestrol, testosterone propionate,fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, and thioguanine.

As used herein, "antibiotics" are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins.

As used herein, "anti-viral agents" are substances capable of destroying or suppressing the replication of viruses. Examples of anti-viral agents include a-methyl-P-adamantanemethylamine, 1,-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, and adenine arabinoside.

As used herein, "enzyme inhibitors" are substances which inhibit an enzymatic reaction. Examples of enzyme inhibitors include edrophonium chloride, N-methylphysostigmine, neostigmine bromide, physostigmine sulfate,tacrine HCl, tacrine, 1-hydroxy maleate, iodotubercidin,p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N6-monomethyl-L-arginine acetate, carbidopa, 3-hydroxybenzylhydrazine HCl, hydralazine HCl, clorgyline HCl, deprenylHCl, L(−)-, deprenylHCl, D(+)-, hydroxylamine HCl, iproniazid phosphate, 6-MeO-tetrahydro-9H-pyridoindole, nialamide, pargylineHCl, quinacrineHCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4, 5-tetrahydro-1H-2-benzazepine hydrochloride, p-aminoglutethimide, p-aminoglutethimide tartrate, R(+)-, p-aminoglutethimide tartrate, S(−)-, 3-iodotyrosine, alpha-methyltyrosine, L-, alpha-methyltyrosine, D L-, acetazolamide, dichlorphenamide, 6-hydroxy-2-benzothiazolesulfonamide, and allopurinol.

As used herein, "neurotoxins" are substances that have a toxic effect on the nervous system, e.g. on nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1, 2,3,6-tetrahydro-pyridine hydrochloride, 1-methyl-4-phenyl-2,3-dihydropyridinium perchlorate, N-methyl-4-phenyl-1,2,5,6tetrahydropyridine HCl, 1-methyl-4-phenylpyridinium iodide.

As used herein, "opioids" are substances having opiate-like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlornaltrexamine2HCl, funaltrexamione HCl, nalbuphine HCl,nalorphine HCl, naloxone HCl, naloxonazine, naltrexone HCl, andnaltrindole HCl.

As used herein, "hypnotics" are substances, which produce a hypnotic effect. Hypnotics include pentobarbital sodium, phenobarbital, secobarbital, thiopental and mixtures thereof, heterocyclichypnotics, dioxopiperidines, glutarimides, diethyl isovaleramide, a-bromoisovaleryl urea, urethanes and disulfanes.

As used herein, "antihistamines" are substances which competitively inhibit the effects of histamines. Examples include pyrilamine, chlorpheniramine, tetrahydrazoline, and the like.

As used herein, "lubricants" are substances that increase the lubricity of the environment into which they are delivered. Examples of biologically active lubricants include water and saline.

As used herein, "tranquilizers" are substances which provide a tranquilizing effect. Examples of tranquilizers include chloropromazine, promazine, fluphenzaine, reserpine, deserpidine, and meprobamate.

As used herein, "anti-convulsants" are substances which have an effect of preventing, reducing, or eliminating convulsions. Examples of such agents include primidone, phenytoin, valproate, Chk and ethosuximide.

As used herein, "muscle relaxants" and "anti-Parkinson agents" are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

As used herein, "anti-spasmodics" and "muscle contractants" are substances capable of preventing or relieving muscle spasms or contractions. Examples of such agents include atropine, scopolamine, oxyphenonium, and papaverine.

As used herein, "miotics" and "anti-cholinergics" are compounds which cause bronchodilation. Examples include echothiophate, pilocarpine, physostigmine salicylate, diisopropylfluorophosphate, epinephrine, neostigmine, carbachol, methacholine, bethanechol, and the like.

As used herein, "anti-glaucoma compounds" are compounds for the prevention or treatment of glaucoma, and include betaxalol, pilocarpine, timolol, timolol salts, and combinations of timolol, and/or its salts, with pilocarpine.

As used herein, "anti-parasitics", "anti-protozoals", and "anti-fungals" are compounds for the prevention or treatment of infestations of parasites, protozoa, and fungi, and include ivermectin, pyrimethamine, trisulfapyrimidine, clindamycin, amphotericin B, nystatin, flucytosine, natamycin, and miconazole.

As used herein, "anti-hypertensives" are substances capable of counteracting high blood pressure. Examples of such substances include alpha-methyldopa and the pivaloyloxyethyl ester of alpha-methyldopa.

As used herein, "analgesics" are substances capable of preventing, reducing, or relieving pain. Examples of analgesics include morphine sulfate, codeine sulfate, meperidine, and nalorphine.

As used herein, "anti-pyretics" are substances capable of relieving or reducing fever, and "anti-inflammatory agents" are substances capable of counteracting or suppressing inflammation. Examples of such substances include aspirin (salicylic acid), indomethacin, sodium indomethacintrihydrate, salicylamide, naproxen, colchicines, fenoprofen, sulindac, diflunisal, diclofenac, indoprofen and sodium salicylamide.

As used herein, "local anesthetics" are substances which have an anesthetic effect in a localized region. Examples of such anesthetics include procaine, lidocaine, tetracaine and dibucaine.

As used herein, "ophthalmics" include diagnostic agents such as sodium fluorescein, rose bengal, methacholine, adrenaline, cocaine, and atropine. Ophthalmic surgical additives include alpha-chymotrypsin and hyaluronidase.

As used herein, "prostaglandins" are an art-recognized class of naturally occurring chemically related, long-chain hydroxy fatty acids that have a variety of biological effects.

As used herein, "anti-depressants" are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

As used herein, "anti-psychotic substances" are substances which modify psychotic behavior. Examples of such agents include phenothiazines, butyrophenones and thioxanthenes.

As used herein, "anti-emetics" are substances which prevent or alleviate nausea or vomiting. An example of such a substance is dramamine.

As used herein, "imaging agents" are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

As used herein, "specific targeting agents" include agents capable of delivering a therapeutic agent to a desired site, e.g., a tumor, and providing a therapeutic effect. Examples of targeting agents include agents which can carry toxins or other agents which provide beneficial effects. The targeting agent can be an antibody linked to a toxin, e.g., ricin A, or an antibody linked to a drug.

As used herein, "neurotransmitters" are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

As used herein, "cell response modifiers" are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein. Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenic proteins including all BMPs.

The term "shaped," as applied to the osteoimplant herein, refers to a determined or regular form or configuration, in contrast to an indeterminate or vague form or configuration (as in the case of a lump or other solid mass of no special form) and is characteristic of such materials as sheet, plate, particle, sphere, hemisphere strand, coiled strand, capillary network, film, fiber, mesh, disk, cone, portion of a cone, pin, screw, tube, cup, tooth, tooth root, strut, wedge, portion of wedge, cylinder, threaded cylinder, rod, hinge, rivet, anchor, spheroid, ellipsoid, oblate spheroid, prolate ellipsoid, hyperbolic paraboloid, and the like.

The phrase "wet compressive strength," as utilized herein, refers to the compressive strength of the osteoimplant after the osteoimplant has been immersed in physiological saline (water containing 0.9 g NaCl/100 ml water) for a minimum of 12 hours. Compressive strength is a well-known measurement of mechanical strength and is measured using the procedure described herein.

The terms "osteogenic," or "osteopromotive," as applied to the osteoimplant of this invention, shall be understood as referring to the ability of the osteoimplant to enhance or accelerate the ingrowth of new bone tissue by one or more mechanisms such as osteogenesis, osteoconduction and/or osteoinduction.

The term "osteopermissive," as applied to the osteoimplant of this invention, shall be understood as referring to the ability of the osteoimplant to not impede the ingrowth of new bone tissue by one or more mechanisms such as osteogenesis, osteoconduction and/or osteoinduction.

As utilized herein, the phrase "superficially demineralized" as applied to bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, for example, less than about 1, weight percent of their original inorganic mineral content. The unmodified term "demineralized" as applied to the bone particles is intended to cover any one or combination of the foregoing types of demineralized bone particles.

Unless otherwise specified, all material proportions used herein are in weight percent.

The term "polyisocyanate," as that term is used herein, encompasses any chemical structure comprising two or more cyanate groups. A "diisocyanate," as used herein, is a subset of the class of polyisocyanates, a chemical structure containing exactly two cyanate (—CN) groups. Similarly, a "polyol" contains two or more alcohol (—OH) groups, while a "diol" contains exactly two alcohol groups.

The term "polyurethane," as used herein, is intended to include all polymers incorporating more than one urethane group (—NH—CO—O—) in the polymer backbone. Polyurethanes are commonly formed by the reaction of a polyisocyanate (such as a diisocyanate) with a polyol (such as a diol):

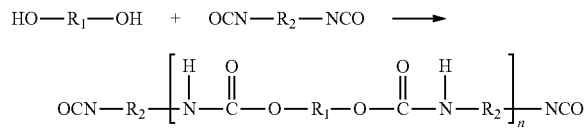

Polyurethanes may be straight chains or branched, and may have high or low molecular weights. The $R_1$ and $R_2$ groups provide great flexibility in tailoring the mechanical and chemical properties of polyurethanes, which may be made rigid, soft, plastic, and/or elastomeric by selection of appropriate functional groups.

As used herein, the term "composite" refers to a mixture of two or more different materials, denominated "matrix" and "reinforcement." Multiple reinforcement materials may be present in a single composite. The term "reinforcement" is not intended to limit or describe any mechanical properties of a material so denominated or its contribution to the mechanical properties of the composite. While the material denominated as the "matrix" may act as a binder to hold together particles, fibers, or fragments of reinforcement material(s), it is not required that the matrix material be fully interconnected throughout the composite; neither is it assumed that the reinforcement material is or is not interconnected throughout the composite. The terms "matrix" and "reinforcement" are also not limited by the fraction of each material present in the composite.

DETAILED DESCRIPTION OF CERTAIN PREFERRED EMBODIMENTS

According to the present invention, polyurethane materials are formed by adding an appropriate polyisocyanate crosslinker (e.g., a diisocyanate) to biomolecules such as lipids (e.g., phospholipids, lecithin, fatty acids, or cholesterols, any of which may be hydroxylated to improve polymerization) polysaccharides (e.g., oligosaccharides or amylase-resistant starches), and/or bone. These polyurethane materials may be mixed with calcium carbonate, calcium sulfate, calcium phosphosilicate, sodium phosphate, calcium aluminate, calcium phosphate, calcium carbonate, hydroxyapatite, other ceramics, or bone, to form composites, which preferably have osteopromotive, osteogenic, and/or osteoinductive properties. Details of traditional polyurethane synthesis can be found, for example, in Lamba, et al., Polyurethanes in biomedical applications, CRC Press, 1998, which is incorporated herein by reference, and particularly in chapter 2 of the above reference.

It is preferred that the polyurethane component of the composite reaction be resorbable and biocompatible. Zhang et al. have synthesized a lysine diisocyanate ethyl ester which they have found to be biocompatible (see Zhang, et al., "A new peptide-based urethane polymer: synthesis, biodegradation, and potential to support cell growth in vitro," *Biomaterials* 21: 1247-1258 (2000), and Zhang, et al., "Synthesis, Biodegradability, and Biocompatibility of Lysine Diisocyanate-Glucose Polymers," *Tis. Eng.*, 8(5): 771-785 (2002), both of which are incorporated herein by reference). Polyurethanes made from this diisocyanate or any other polyisocyanate (e.g., toluene diisocyanate, arginine diisocyanate, asparagine diisocyanate, proline diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, aliphatic, alicyclic, or aromatic polyisocyanates) that are degradable by the host and does not have undesirable toxic effects in vivo may be used to prepare the polyurethanes and composites of the invention.

The polyol component of the polyurethane of the invention is a biomolecule, which may be hydroxylated by standard methods if it does not already possess sufficient hydroxyl groups to carry out a reaction. For example, lipids, including phospholipids, mono-, di-, and triglycerides, fatty acids, and cholesterols, may require addition of hydroxyl groups in order to carry out the polymeriztion reaction. In contrast, polysaccharides such as starches typically already have sufficient hydroxyl groups to polymerize readily into a highly cross-linked polymer. The biomolecule polyol may be mixed with other polyols. For example, poly(c-caprolactone) is a common additive when synthesizing polyurethane block copolymers, and may also be used in the present invention. Other polycaprolactones may also be either copolymerized or blended into the final polymer, as may other appropriate polymers.

When a diol is reacted with a diisocyanate, a polyurethane with minimal crosslinking is generally formed. Such polymers are generally thermoplastic and readily deformable, and may be subject to strain-induced crystallization for hardening. In contrast, if at least some of either the polyol or the polyisocyanate comprises at least three active groups participating in the reaction, then the polymer will generally be heavily cross-linked. Such polymers are typically thermosets, and tend to be harder than polymers with low cross-linking. In addition, their mechanical properties tend to be less dependent on how they are processed, which may render them more machinable.

Because the reaction process combines an isocyanate with a biological molecule, any breakdown products of the polymer are generally biocompatible and preferably resorbable. It is preferred that the polyurethanes of the invention be enzymatically degradable, bioerodable, hydrolytically stable, and/or bioabsorbable. Thus, when an osteoimplant is formed from the materials of the invention, it can be slowly replaced by the ingrowth of natural bone as the implant degrades. This process of osteogenesis may be accelerated, for example, by the addition of bioactive agents. Such bioactive agents may be incorporated into the polymer structure, either as backbone elements or as side groups, or they may be present as solutes in the solid polymer or as non-covalently bonded attachments. In any case, they may be gradually released as the polyurethane degrades. The rate of release may be tailored by modifying the attachment or incorporation of the bioactive agents into the polymer. Bioactive agents that may be used include not only agents having osteogenic properties, but also agents having other biological properties such as immunosuppression, chemoattraction, or those listed in Appendix A. Lectins are a class of particular interest for incorporation into the present polymers, especially when the polymers comprise carbohydrates, which bond readily to lectins.

In some embodiments, it is preferred that the polyurethanes of the invention be enzymatically degradable, bioerodable, hydrolytically stable, and/or bioabsorbable. Thus, when an osteoimplant formed from the materials of the invention degrades, any byproducts of the enzymatic process or bioerosion may be biocompatible and may be utilized in or may be metabolites in any cellular metabolic pathway, such as but not limited to cellular respiration, glycolysis, fermentation, or the tricarboxylic acid cycle.

For certain applications, it may be desirable to create foamed polyurethane, rather than solid polyurethane. While typical foaming agents such as hydrochlorofluoro-carbons, hydrofluorocarbons, and pentanes may not be biocompatible for many systems, other, biocompatible agents may be used. For example, Zhang et al. have found that water may be an adequate foaming agent for a lysine diisocyanate/PEG/glycerol polyurethane (see Zhang, et al., "Three-dimensional biocompatible ascorbic acid-containing scaffold for bone tissue engineering," supra). Other foaming agents include dry ice or other agents which release carbon dioxide or other gases into the composite.

Whether foamed or solid, polyurethanes according to the invention may be formed into a composite with bone particulates (optionally demineralized), or with bone substitutes such as calcium carbonate, calcium sulfate, calcium phosphosilicate, sodium phosphate, calcium aluminate, calcium phosphate, calcium carbonate, hydroxyapatite, or other ceramics. In addition, collagen may also be formed into a composite with the polyurethane, with or without the addition of bone. The treatment of bone particles for incorporation into composites is discussed below. It is noted that natural bone, hydroxyapatite, and collagen may bond strongly to the isocyanates used in forming the polymer, since they contain significant numbers of active hydroxyl groups. Thus, it may be preferred in some embodiments to first mix the bone, hydroxyapatite, and/or collagen with the polyol monomer, before addition of the isocyanate. Nevertheless, it is also within the scope of the invention to mix the reinforcing material into already-combined polyol and isocyanate, or to combine all three components simultaneously.

The polyurethanes and composites of the invention preferably have a sufficient wet compressive strength to provide mechanical stability for an osteoimplant during healing. In addition, they preferably have low creep rates and good fatigue resistance. For example, wet compressive strengths of at least 3 MPa, 10 MPa, or 50 MPa are preferred, with strengths of at least 75 MPa or 100 MPa being even more desirable. Creep rates of less than 10% per 24 hours at 25 MPa (wet) are preferred, as is fatigue resistance of at least $10^6$ cycles at 25 MPa (wet). However, even if these mechanical properties are not present in the polymer or composite, the polymers and composites of the invention can be combined with other materials or used alone in osteoimplants according to the invention. In some preferred embodiments, the mechanical strengeth, elastic modulus, and anisotropic properties of the implant can be tailored by adjusting the polymer chain length distribution, side chain length, degree of cross-linking, and/or physical processing.

Preparation of Bone for Incorporation Into Composites

The bone particles employed in the preparation of the bone particle-containing composition can be obtained from cortical, cancellous, and/or corticocancellous bone which may be of autogenous, allogenic and/or xenogeneic origin and may or may not contain cells and/or cellular components. Preferably, the bone particles are obtained from cortical bone of allogenic origin. Porcine and bovine bone are particularly advantageous types of xenogeneic bone tissue that can be used individually or in combination as sources for the bone particles. Particles are formed by milling whole bone to produce fibers, chipping whole bone, cutting whole bone, fracturing whole bone in liquid nitrogen, or otherwise disintegrating the bone tissue. Particles can optionally be sieved to produce particles of a specific size.

The bone particles employed in the composition can be virtually any fragment or portion of a whole bone, such as powdered bone particles possessing a wide range of particle sizes ranging from relatively fine powders to coarse grains and even larger chips, cubes, shards, or fibers. In one embodiment, bone particles can range in average particle size from about 0.05 mm to about 1.2 mm and possess a median length to median thickness ratio of from about less than 1:1 to about greater than 10:1. In another embodiment, bone particles can range in average particle size from about 0.005 mm to about 10 mm and possess a median length to median thickness ration from about less than 1:1 to about greater than 100:1. If desired, powdered bone particles can be graded into different sizes to reduce or eliminate any less desirable size(s) of particles that may be present. The combination of bone particles and a polymer both reduces the amount of bone that is required to prepare the implant and eliminates shape constraints on the bone itself, since the polymer and composite may be molded into any desired shape.

Alternatively, or in combination with the aforementioned bone powder, bone particles generally characterized as elongate and possessing relatively high median length to median thickness ratios can be utilized herein. Such elongate particles can be readily obtained by any one of several methods, e.g., by milling or shaving the surface of an entire bone or relatively large section of bone. Employing a milling technique, one can obtain a mass of elongate bone particles containing, for example, at least about 60 weight percent of elongate bone particles possessing a median length of from about 2 to about 200 mm or more, a median thickness of from about 0.05 to about 2 mm, and a median width of from about 1 mm to about 20 mm. Such elongate bone particles can possess a median length to median thickness ratio of at least about 50:1 up to about 500:1 or more and a median length to median width ratio of from about 10:1 to about 200:1. The milling process may be optimized to adjust the size of the bone particles and the size distribution, and virtually any fragment or portion of a whole bone could be made by the milling process. The mechanical strength, elastic modulus, and anisotropy of the implant can be tailored by adjusting the weight percent of the various shapes (elongate, particulate, etc.) of bone particles utilized in the composite.

Another procedure for obtaining elongate bone particles, particularly useful for pieces of bone of up to about 100 mm in length, is the bone processing mill described in commonly assigned U.S. Pat. No. 5,607,269, the entire contents of which are incorporated herein by reference. Use of this bone mill results in the production of long, thin strips that quickly curl lengthwise to provide tubular-like bone particles. If desired, elongate bone particles can be graded into different sizes to reduce or eliminate any less desirable size(s) of particles that may be present. In overall appearance, elongate bone particles can be described as filaments, fibers, threads, slender or narrow strips, etc.

The bone particles are optionally demineralized in accordance with known and conventional procedures in order to reduce their inorganic mineral content. Demineralization methods remove the inorganic mineral component of bone, for example by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape of the bone particles and the duration of the demineralization treatment will determine the extent of demineralization. Reference in this regard may be made to Lewandrowski, et al., *J. Biomed. Mater. Res.*, 1996, 31: 365-372, the contents of which are also incorporated herein by reference.

In a preferred demineralization procedure, the bone particles are subjected to a defatting/disinfecting step, followed by an acid demineralization step. A preferred defatting/disinfectant solution is an aqueous solution of ethanol. Ethanol is a good solvent for lipids, and water is a good hydrophilic carrier that enables the solution to penetrate more deeply into the bone particles. Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. The acid also disinfects the bone by killing viruses, vegetative microorganisms, and spores. Acids that can be employed in this step include inorganic acids such as hydrochloric acid and organic acids such as peracetic acid. After acid treatment, the demineralized bone particles are rinsed with sterile water to remove residual amounts of acid and thereby raise the pH. The bone particles are preferably dried, for example, by lyophilization, before incorporated into the composite. The bone particles may be stored under aseptic conditions until they are used or sterilized using known methods shortly before combining them with the monomer.

Mixtures or combinations of one or more of the above types of bone particles can be employed. For example, one or more of the foregoing types of demineralized bone particles can be employed in combination with nondemineralized bone particles, i.e., bone particles that have not been subjected to a demineralization process. The demineralized bone particles may behave as short fibers in the composite, acting to increase fracture toughness. The nondemineralized bone particles may behave as ceramic inclusions, increasing the compressive strength of the composite. Nondemineralized bone is itself a fiber-reinforced composite, which may increase the bending and tensile stress the composite can withstand before the bone particles break. Superficial demineralization produces particles containing a mineralized core. Particles of this type may behave as non-demineralized particles in the composite, depending on the degree on demineralization.

Bone particles may either be used without lyophilization or lyophilized and/or otherwise treated to remove water from the bone. Some preferred embodiments of the described invention include the use of lyophilized bone.

The bone particles in the composite also play a biological role. Non-demineralized bone particles bring about new bone ingrowth by osteoconduction, in which an advancing bone front binds to the particle surface. Demineralized bone particles likewise play a biological role in bringing about new bone ingrowth by osteoinduction, in which bone cells are recruited from the host tissue to regenerate bone at the implant site. Both types of bone particles may be gradually remodeled and replaced by new host bone as degradation of the composite progresses over time. This process is desirable because the load-bearing capacity is gradually transferred from the implant to the new bone growth, thereby reducing the risk of implant failure due to rapid degradation.

EXAMPLES

Example #1

To determine the compressive strength of a composite implant made of approximately 66.6% bone and 33.3% castor bean polyurethane resin; 20 grams of bovine bone powder (particle size 120 μm-500 μm) were combined with a two part polyurethane (Doctors Research Group, Plymouth CT and described in "Vegetal Polyurethane Resin Implant Cranioplasty. Experimental Studies in Rabbits" by Luiz Fernando Francisco, Sao Jose do Rio Preto, 1998, which is incorporated herein by reference). Firstly, 6.10 grams of liquid comprising a polyisocyanate terminated molecule "prepolymer" were combined with 3.60 grams of a liquid comprising castor bean oil fatty acid triglyceride "diol". Next, bone particles were gradually mixed into the polyurethane solution, until the bone appeared well coated. The mixture was then packed by hand into three 5 cc syringes (packed with light hand pressure). The samples were then set aside to polymerize over a 48-hour period at room temperature. After polymerization was complete, the samples were removed from the syringes and cut to length (approx. 16 mm). Of the 4 samples tested; 2 were tested dry, while two were hydrated in Simulated Body Fluid (SBF) for 24 hours and tested wet. (SBF solution contained 7.992-7.998 NaCl, 0.2230-0.2243 g KCl, 0.2275-0.2289 g $K_2HPO_4.3H_2O$, 0.3041-0.3059 g $MgCl_2.6H_2O$, 36-40 ml HCl (1N), 0.3665-0.3687 g $CaCl_2.2H_2O$, 0.0708-0.0712 g $Na_2SO_4$, 0.3517-0.3539 g $NaHCO_3$, and deionized water to make 1000 ml, adjusted to a pH of 7.2-7.4 by a buffer solution of tris (hydroxymethyl)aminomethane). The results of mechanical static compression tests using the Bionix MTS 858 (Edin Prarrie MN) are shown in column 5 of Table 1. Results indicated a slight decrease in compressive strength (of about 7%) with the hydrated implants compared to the compressive strength of the dry implants, but load bearing capacity was still considered acceptable for use as an implant.

TABLE 1

| Sample | Length (mm) | Diameter (mm) | Weight (g) | Compressive Strength (MPa) |
|---|---|---|---|---|
| A-Dry | 16.74 | 11.85 | 2.70 | 72 |
| B-Dry | 16.58 | 11.84 | 2.64 | 72 |
| C-Wet | 16.68 | 11.87 | 2.63 | 66 |
| D-Wet | 16.70 | 11.87 | 2.63 | 67 |

Example #2

To determine the compressive strength of an implant made of 100% two-part castor bean polyurethane resin, (Doctors Research Group, Plymouth Conn. and described in "Vegetal Polyurethane Resin Implant Cranioplasty. Experimental Studies in Rabbits" by Luiz Fernando Francisco, Sao Jose do Rio Preto, 1998) enough of the prepolymer and diol (as indicated in Example 1) were mixed together to fill a 5 cc syringe. The material was hand packed into the syringe and allowed to polymerize for 18 hours at room temperature (air bubbles were noticed within the sample). After polymerization was complete, the samples were removed from the syringe and cut to length (approx. 13 mm).

The results of mechanical static compression tests, using the Bionix MTS 858 (Edin Prarrie Minn.), are shown in column 5 of Table 2. The MPa values listed are only approximate at the point of visible plastic deformation of the implant. Samples did not mechanically fail at 20 MPa, but rather plastically deformed such that the test had to be stopped at approximately 50% strain. The load bearing capacity of the implants was still considered acceptable for use as an implant.

TABLE 2

| Sample ID | Length (mm) | Diameter (mm) | Weight (g) | Approximate Compressive Strength (MPa) |
|---|---|---|---|---|
| A-Dry | 12.96 | 8.55 | .78 | 20 |
| B-Dry | 13.97 | 8.52 | .81 | 20 |

Example #3

To determine the compressive strength of a composite implant made of approximately 75% bone and 25% castor bean polyurethane resin, 20 grams of bovine bone powder (particle size 120 μm-500 μm) were combined with a 6.82 grams of a two part polyurethane (Doctors Research Group, Plymouth CT and described in "Vegetal Polyurethane Resin Implant Cranioplasty. Experimental Studies in Rabbits" by Luiz Fernando Francisco, Sao Jose do Rio Preto, 1998). The mixture was then packed by hand into three 5 cc syringes (packed with light hand pressure). The samples were then set aside to polymerize over a 48-hour period at room temperature. After polymerization was complete, the samples were removed from the syringes and cut to length (approx. 14 mm). Of the 6 samples tested; 4 were tested dry, while two were hydrated in Simulated Body Fluid (SBF) for 24 hours and tested wet. The results of mechanical static compression tests using the Bionix MTS 858 (Edin Prarrie Minn.) are shown in column 5 of Table 3. Results indicated a decrease in compressive strength (of about 21.8%) with the hydrated implants compared to the compressive strength of the dry implants but load bearing capacity was still considered acceptable for use as an implant.

TABLE 3

| Sample ID | Length (mm) | Diameter (mm) | Weight (g) | Compressive Strength (MPa) |
|---|---|---|---|---|
| A1-Dry | 13.92 | 11.88 | 2.03 | 51 |
| A2-Dry | 14.02 | 11.87 | 2.14 | 56 |
| A3-Wet | 12.37 | 11.96 | 1.96 | 43 |
| B1-Dry | 14.16 | 11.86 | 2.25 | 59 |
| B2-Dry | 14.16 | 11.81 | 2.11 | 54 |
| B3-Wet | 14.34 | 11.92 | 2.23 | 43 |

Example #4

To determine if a polyurethane could be made using a lecithin and a castor bean polyurethane resin, 3.0 grams of lecithin powder were combined with a 3.0 grams of liquid comprising a polyisocyanate terminated molecule "prepolymer" (as indicated in Example 1). The mixture was then packed by hand into 5 cc syringes (packed with light hand pressure). While the sample did polymerize, the reaction took more than 48 hours.

Example #5

To determine if composite implant compressive strength could be increased by improving the association and/or number of urethane bonds of the bone particles and the "diol", an implant comprising 73% bone particles and 23% two-part castor bean polyurethane resin, (as in Example 1) was made by first mixing 15 grams of demineralized bone powder (particle size 120 μm-500 μm) with the "diol" as indicated in Example 1. The mixture was allowed to sit for 1 hour to ensure that "the diol" penetrated into the bone. Next, the liquid comprising a polyisocyanate terminated molecule "prepolymer" was mixed into the material and hand packed into 5 cc syringes. After polymerization was complete the material was removed from the syringe, but fell apart. This may have been due to excess diol or lack of sufficient prepolymer. Modifications of this method will result in an implant that maintains its shape and is suitable for implantation.

Example #6

To determine if a polyurethane could be made using a Toluene diisocyanate and a castor bean polyurethane resin, 4.0 grams of a Toluene diisocyanate were combined with 4.0 grams of a liquid comprising castor bean oil fatty acid triglyceride "diol" as indicated in Example 1. The mixture was then packed by hand into 5 cc syringes (packed with light hand pressure). While the sample did partially polymerize, the material was not firm. Addition of a catalyst may increase the rate of and efficiency of polymerization in this example. This example was also performed with 65% Toluene diisocyanate and 35% diol, again the sample did at least partially polymerize. The reaction took more than 48 hours, but the material was not firm.

Example #7

To determine if a polyurethane could be made using a Toluene diisocyanate and a hydroxylated lecithin, 4.0 grams of a Toluene diisocyanate were combined with 4.0 grams of a hydroxylated lecithin. The mixture was then packed by hand into 5 cc syringes (packed with light hand pressure). The sample did at least partially polymerize faster than in Example 6, but the material was not firm.

Example #8

To determine if a polyurethane could be made using a Toluene diisocyanate and a hydroxylated lecithin with the addition of heat to improve the rate of the polymerization, a 50:50 mixture was produced as in Example 7, while being heated to 93-95 degrees Celsius (on hot plate). The material became foamy and flowed over the mixing vessel. Once the material cooled it formed a porous at least partially polymerized sheet.

Example #9

To determine if a polyurethane could be made using a lysine diisocyanate and a hydroxylated lecithin, 6.0 grams of a lysine diisocyanate were combined with 6.0 grams of a hydroxylated lecithin. The mixture was then set at room temperature to polymerize. While the sample did at least partially polymerize with a hard shell after 72 hours, the material was not firm.

Example #10

To determine if a polyurethane could be made using a lysine diisocyanate and a hydroxylated lecithin, 12.0 grams of a lysine diisocyanate were combined with 4.0 grams of a hydroxylated lecithin. The mixture was then set at room temperature to polymerize. While the sample did polymerize very quickly, it swelled up, filled with air bubbles generating foam that developed a hard shell after a few hours.

Example #11

To determine if a composite implant could be made of bone with a lysine diisocyanate and castor bean polyurethane resin; 6 grams of a lysine diisocyanate were combined with 3.50 grams of a liquid comprising castor bean oil fatty acid triglyceride "the diol". Next, the mixture was heated to 93-95 degrees Celsius (on hot plate) and bone particles (particle size 120 μm-500 μm) were gradually mixed into the polyurethane solution, until the bone appeared well coated. The mixture was then packed by hand into 5 cc syringes (packed with light hand pressure). The samples were then set aside to polymerize over a 48-hour period at room temperature. The material polymerized at least partially and could be extruded out of the syringe.

Example #12

3 grams of lysine diisocyanate were mixed with ProGenix Carrier #2 and at least partially polymerized to produce a flexible gel like sheet within a few hours.

Example #13

3 grams of lysine diisocyanate were mixed with 1.5 grams glycerol. After 2 weeks the mixture formed a hard at least partially polymerized film layer.

Example #14

6 grams of lysine diisocyanate were combined with 3 grams of starch carrier B90 and M180 (Grain Processing Corporation, Muscatine, Iowa). When mixture was partially polymerized, 1.5 grams of bone (particle size 120 μm-500 μm) were added to create a slurry. The material was then hand packed into a 5 cc syringe and pressed lightly with plunger. Although the materially may have at least partially polymerized, it remained soft and flexible.

Example #15

To demonstrate polymerization according to the invention, a monomer or monomer combination, is mixed with bone. Desired formulations by weight percent are given in Table 4. Ratios of crosslinker to polymer may be varied according to specific requirements of the desired biomaterial over a wide range, at least from about 10:1 to 1:10. A conventional polymerization catalyst known to those skilled in the art (such as an amine or tin compound) may or may not also be added, and the mixture is then combined with the crosslinking agent indicated and placed in a mold (such as Teflon) to polymerize. The percentage of the final composite comprised of composite filler (i.e., bone) may be varied between 5% and 95% according to the specific requirements of the biomaterial. The mixture polymerizes to form a bone-polyurethane composite. In one preferred embodiment calcium phosphate granules are substituted for the bone portion of the formulation. Exemplary preparations of calcium phosphates are described by U.S. Pat. No. 5,650,176 to Lee et al., U.S. Pat. No. 6,002,065 to Constantz et al., and U.S. Pat. No. 6,206,957 to Driessens et al., all of which are incorporated by reference herein.

TABLE 4

| Formulation number | Monomer (wt %) | Crosslinker (wt %) | Reinforcement |
|---|---|---|---|
| 1 | Lecithin | Hexamethylene | Cortical bone |
| 2 | Starch | Diisocyanate | particles (200- |
| 3 | Starch:Lecithin 15:85 | | 1000 microns) |
| 4 | Starch:Lecithin 85:15 | | |
| 5 | Collagen | | |
| 6 | Lecithin | Uretdione | |
| 7 | Starch | polyisocyanate | |
| 8 | Starch:Lecithin 15:85 | | |
| 9 | Starch:Lecithin 85:15 | | |
| 10 | Collagen | | |
| 11 | Lecithin | 1,4 butane | |
| 12 | Starch | diisocyanate | |
| 13 | Starch:Lecithin 15:85 | | |
| 14 | Starch:Lecithin 85:15 | | |
| 15 | Collagen | | |
| 16 | Lecithin | Hexamethylene | Surface |
| 17 | Starch | diisocyanate | demineralized |
| 18 | Starch:Lecithin 15:85 | | bone particles |
| 19 | Starch:Lecithin 85:15 | | |
| 20 | Collagen | | |
| 21 | Lecithin | Uretdione | |
| 22 | Starch | polyisocyanate | |
| 23 | Starch:Lecithin 15:85 | | |
| 24 | Starch:Lecithin 85:15 | | |
| 25 | Collagen | | |
| 26 | Lecithin | 1,4 butane | |
| 27 | Starch | diisocyanate | |
| 28 | Starch:Lecithin 15:85 | | |
| 29 | Starch:Lecithin 85:15 | | |
| 30 | Collagen | | |
| 31 | Lecithin | Hexamethylene | Calcium |
| 32 | Starch | diisocyanate | Phosphate |
| 33 | Starch:Lecithin 15:85 | | |
| 34 | Starch:Lecithin 85:15 | | |
| 35 | Collagen | | |
| 36 | Lecithin | Uretdione | |
| 37 | Starch | polyisocyanate | |
| 38 | Starch:Lecithin 15:85 | | |
| 39 | Starch:Lecithin 85:15 | | |
| 36 | Collagen | | |
| 37 | Lecithin | 1,4 butane | |
| 38 | Starch | diisocyanate | |
| 39 | Starch:Lecithin 15:85 | | |
| 40 | Starch:Lecithin 85:15 | | |
| 41 | Collagen | | |

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A biodegradable polyurethane composite, comprising: a polyurethane matrix formed by reaction of a polyisocyanate with a hydroxylated biomolecule to form a biodegradable polyurethane polymer; and a reinforcement embedded in the matrix, wherein the reinforcement comprises bone and bone substitutes.

2. A biodegradable polyurethane, formed by reaction of a polyisocyanate with a mixture of hydroxylated biomolecules to form a polyurethane polymer, wherein the mixture of hydroxylated biomolecules comprises polysaccharides; and lipids or phospholipids.

3. The polyurethane of claim 2, wherein the polymer is cross-linked.

4. The polyurethane of claim 2, wherein the polyisocyanate is a diisocyanate.

5. The polyurethane of claim 2, wherein the polyisocyanate is selected from the group consisting of lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, and aliphatic, alicyclic, and aromatic polyisocyanates.

6. The polyurethane of claim 2, wherein the mixture of biomolecule comprises lecithin.

7. The polyurethane of claim 2, further comprising polycaprolactone.

8. The polyurethane of claim 2, further comprising a substance selected from a biomolecule, a bioactive agent, and a small molecule.

9. The polyurethane of claim 8, wherein the substance is selected from the group consisting of lectins, growth factors, immunosuppressives, and chemoattractants.

10. The polyurethane of claim 2, further comprising a reinforcement embedded in a matrix of the polyurethane to form a composite material.

11. The polyurethane of claim 10, wherein the reinforcement comprises a material is selected from the group consisting of calcium carbonate, calcium sulfate, calcium phosphosilicate, sodium phosphate, calcium aluminate, calcium phosphate, calcium carbonate, hydroxyapatite, demineralized bone, mineralized bone, and combinations and modified forms of the above.

12. The polyurethane of claim 10, comprising at least 10 weight percent of the reinforcement.

13. The polyurethane of claim 10, comprising at least 30 weight percent of the reinforcement.

14. The polyurethane of claim 10, comprising at least 50 weight percent of the reinforcement.

15. The polyurethane of claim 10, comprising at least 70 weight percent of the reinforcement.

16. The polyurethane of claim 10, wherein the composite material has a wet compressive strength that exceeds the wet compressive strength of the polyurethane alone.

17. The polyurethane of claim 2, wherein the polyurethane has a wet compressive strength of at least 3 MPa.

18. The polyurethane of claim 2, wherein the polyurethane has a wet compressive strength of at least 10 MPa.

19. The polyurethane of claim 2, wherein the polyurethane has a wet compressive strength of at least 50 MPa.

20. The polyurethane of claim 2, wherein the polyurethane has a wet compressive strength of at least 75 MPa.

* * * * *